(12) United States Patent
Alsafadi et al.

(10) Patent No.: US 8,979,756 B2
(45) Date of Patent: Mar. 17, 2015

(54) WIRELESS MEDICAL MONITORING DEVICE

(75) Inventors: Yasser Alsafadi, Yorktown Heights, NY (US); Walid S. I. Ali, Chandler, AZ (US)

(73) Assignee: Koninklijke Philips N.V., Eindhoven (NL)

( * ) Notice: Subject to any disclaimer, the term of this patent is extended or adjusted under 35 U.S.C. 154(b) by 1779 days.

(21) Appl. No.: 11/913,496

(22) PCT Filed: Apr. 28, 2006

(86) PCT No.: PCT/IB2006/051345
§ 371 (c)(1),
(2), (4) Date: Nov. 2, 2007

(87) PCT Pub. No.: WO2006/120600
PCT Pub. Date: Nov. 16, 2006

(65) Prior Publication Data
US 2008/0194925 A1    Aug. 14, 2008

Related U.S. Application Data

(60) Provisional application No. 60/678,685, filed on May 6, 2005.

(51) Int. Cl.
*A61B 5/00* (2006.01)
*G06Q 50/22* (2012.01)
*H04B 13/00* (2006.01)

(52) U.S. Cl.
CPC ............. *A61B 5/0002* (2013.01); *A61B 5/0024* (2013.01); *A61B 5/0028* (2013.01); *A61B 5/411* (2013.01); *G06Q 50/22* (2013.01); *H04B 13/005* (2013.01); *A61B 5/7264* (2013.01)
USPC ............................ 600/301; 600/300; 607/60

(58) Field of Classification Search
None
See application file for complete search history.

(56) References Cited

U.S. PATENT DOCUMENTS 5,730,124 A * 3/1998 Yamauchi ................... 600/300
6,409,661 B1    6/2002 Murphy
(Continued)

FOREIGN PATENT DOCUMENTS

EP        0707824 A2    4/1996
JP        9075309 A     3/1997
(Continued)

OTHER PUBLICATIONS

Ali, W., et al., "Identifying Artifacts in Arterial Blood Pressure Using Morphogram Variability", Philips Research USA, Briarcliff Manor, NY, USA; 4 pgs.
(Continued)

*Primary Examiner* — Gary Jackson
*Assistant Examiner* — Bobby Soriano

(57) ABSTRACT

Described herein is a patient monitoring system that includes a body network (16) with at least one sensor (12) that senses physiological information about a patient and a cognitive device (2) for communicating the physiological information to a remote location. The cognitive device includes a cognitive radio (4), a cognitive monitor (10), and a transmitter (8). The cognitive radio (4) checks detected frequency spectra (6) for unused bandwidth and recommends one or more bands on which to transmit clinically relevant information received from the body network (16) to the remote location; the cognitive monitor (10) receives the information from the body network (16), prioritizes the information based at least in part on a set of rules (30), and selects which information to transmit based on the prioritization and the recommended transmission bands; and the transmitter (8) transmits the selected information as a junction of priority over at least one or the recommended transmission bands.

19 Claims, 5 Drawing Sheets

(56) References Cited

U.S. PATENT DOCUMENTS

| | | | |
|---|---|---|---|
| 6,720,887 B1 * | 4/2004 | Zunti | 340/870.28 |
| 7,130,678 B2 * | 10/2006 | Ritscher et al. | 600/523 |
| 7,130,687 B2 * | 10/2006 | Cho et al. | 607/17 |
| 7,171,161 B2 * | 1/2007 | Miller | 455/67.11 |
| 7,218,969 B2 * | 5/2007 | Vallapureddy et al. | 607/60 |
| 7,254,191 B2 * | 8/2007 | Sugar et al. | 375/340 |
| 7,408,907 B2 * | 8/2008 | Diener | 370/338 |
| 7,424,268 B2 * | 9/2008 | Diener et al. | 455/62 |
| 2002/0045920 A1 * | 4/2002 | Thompson | 607/60 |
| 2002/0193076 A1 * | 12/2002 | Rogers et al. | 455/66 |
| 2002/0198473 A1 | 12/2002 | Kumar et al. | |
| 2004/0028003 A1 * | 2/2004 | Diener et al. | 370/319 |
| 2004/0047324 A1 * | 3/2004 | Diener | 370/338 |
| 2004/0146149 A1 | 7/2004 | Rogers | |
| 2004/0259563 A1 * | 12/2004 | Morton et al. | 455/452.2 |
| 2006/0084444 A1 * | 4/2006 | Kossi et al. | 455/450 |
| 2006/0221918 A1 * | 10/2006 | Wang | 370/338 |
| 2006/0241512 A1 * | 10/2006 | Kwok et al. | 600/547 |
| 2007/0075803 A1 * | 4/2007 | Kemmochi et al. | 333/132 |
| 2007/0213084 A1 * | 9/2007 | Birru et al. | 455/501 |

FOREIGN PATENT DOCUMENTS

| | | |
|---|---|---|
| JP | 2000083917 A | 3/2000 |
| WO | 03101289 A1 | 12/2003 |
| WO | 2004084720 A2 | 10/2004 |

OTHER PUBLICATIONS

Federal Communications Commission, Notice of Proposed Rule Making and Order, FCC 03-322 Released Dec. 30, 2003, "Facilitating Opportunities for Flexible, Efficient, and Reliable Spectrum Use Employing Cognitive Radio Technologies", "Authorization and Use of Software Defined Radios", 53 pgs.

Frost & Sullivan; "U.S. Emerging Wireless Markets for Patient Care—A700-48", ©2004 Frost & Sullivan; www.frost.com.

Mangold, S., et al.; Spectrum Agile Radio: Radio Resource Measurements for Opportunistic Spectrum Usage; 2004; Global Communications Conference-Globecom-IEEE; vol. 6; pp. 3467-3471.

Xio, Y.; IEEE 802.11E: Q0S Provisioning at the MAC Layer; 2004; IEEE Wireless Communications; 11(3)72-79.

* cited by examiner

WIRELESS MEDICAL MONITORING DEVICE

CROSS REFERENCE TO RELATED APPLICATIONS

This application claims the benefit of U.S. provisional application Ser. No. 60/678,685 filed Nov. 2, 2005, which is incorporated herein by reference.

The following relates to monitoring a person's physiological state. It finds particular application to wireless body networks and, more particularly, to conveying at least a subset of physiological data signals via previously allocated spectra to a monitoring system. Some aspects are also applicable for general wellness monitoring.

Patients have traditionally been monitored using sensing units connected by wires to a base unit. These wires inhibited patient mobility and were labor intensive to install. To facilitate installation and eliminate wire clutter, wireless sensing units have been developed. Wireless units also enable the patient to move around the room and possibly the ward or the hospital. Outpatients were similarly limited to a convalescent room or possibly their home. Many outpatients, while needing monitoring are well enough to move about the community, but to do so they had to move about unmonitored. Although higher powered wireless monitors are theoretically possible, there are radio frequency communication spectrum problems. Particularly, there is a shortage of frequency bands, and existing bands are crowded.

Spectrum access, use, efficiency, and reliability are critical public policy issues. In response to the increasing demand for spectrum use within a domain of a finite number of frequency bands, the United States Federal Communications Commission (FCC) is looking at proposed rule changes that will allow third parties to use a portion of a previously allocated spectrum when that portion is not being utilized by the controlling party. Currently, they have divided the communications frequency spectrum into many bands that have been allocated, leased or sold to specific users/industries (e.g., radio, television, wire, satellite and cable). The quantity and quality of unused previously allocated spectrum available to third parties and the duration that such spectrum will be available (e.g., remain unused) will vary from allocated party to allocated party.

The following relates to a patient monitoring system that includes a body network with at least one sensor that senses physiological information about a patient and a cognitive device for communicating the physiological information to a remote location. The cognitive device includes a cognitive radio, a cognitive monitor, and a transmitter. The cognitive radio checks detected frequency spectra for unused bandwidth and recommends one or more bands on which to transmit clinically relevant information received from the body network to the remote location; the cognitive monitor receives the information from the body network, prioritizes the information based at least in part on a set of rules, and selects which information to transmit based on the prioritization and the recommended transmission bands; and the transmitter transmits the selected information as a function of priority over at least one or the recommended transmission bands.

One advantage includes wirelessly communicating signals from a wireless Body Area Network (BAN) over previously allocated but unused spectrum for monitoring by a clinician.

Another advantage resides in enabling extended patient monitoring outside the hospital with minimal modification to their lifestyle.

Another advantage is wireless monitoring that can be deployed anywhere in the world with minimal configuration.

Another advantage resides in reducing the numerous wires between a patient, monitoring systems, and associated displays.

Another advantage resides in an alternative for managing disease and outpatient care.

Still further advantages will become apparent to those of ordinary skill in the art upon reading and understanding the detailed description of the preferred embodiments.

Figure 1:
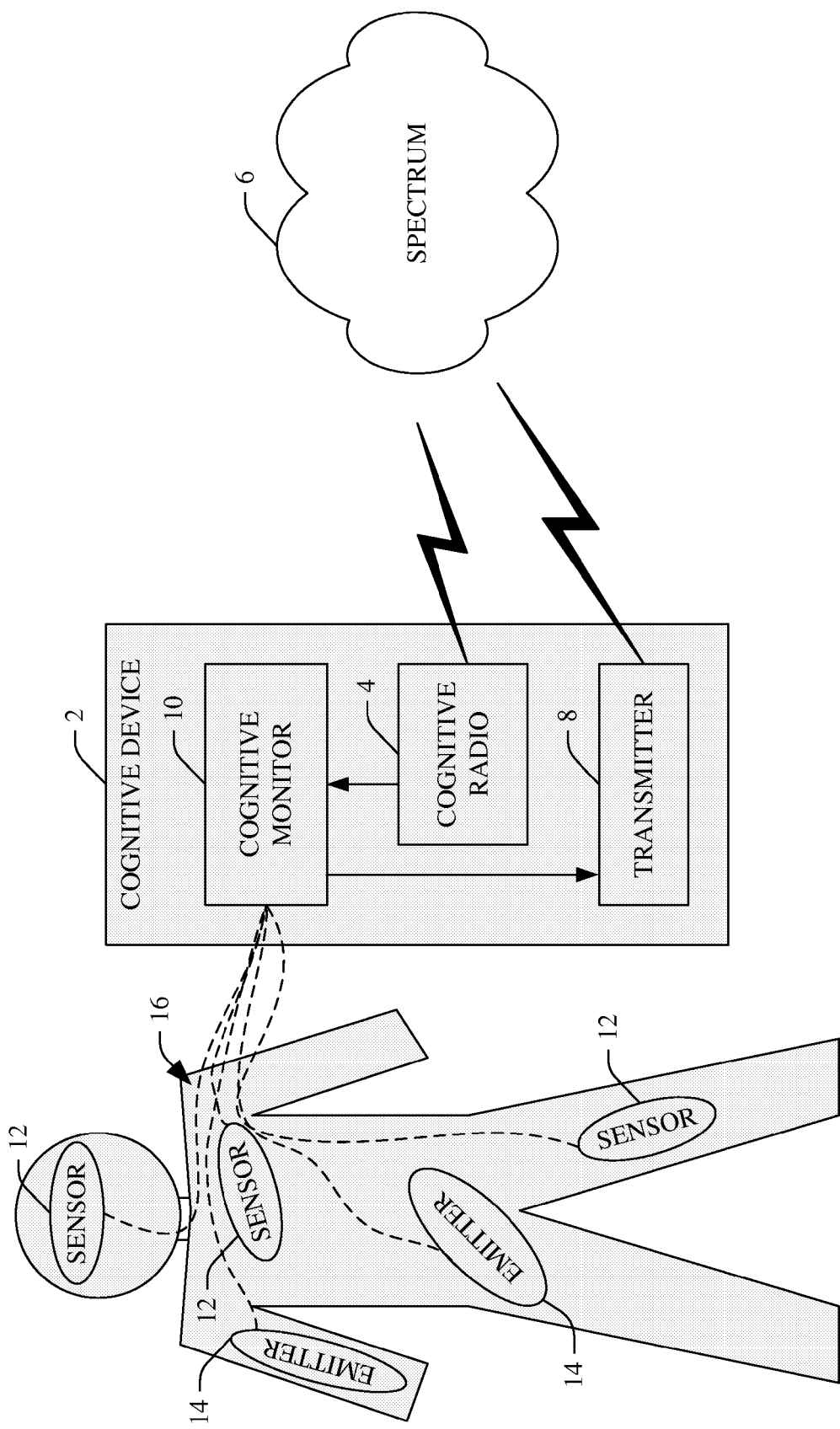
FIG. 1 illustrates a cognitive (spectrum agile) device for receiving and selectively conveying signals from one or more monitoring devices residing within a wireless body network.

FIG. 1 illustrates a cognitive (spectrum agile) device 2 for receiving and selectively conveying signals from one or more monitoring devices residing within a wireless body network. The cognitive device 2 includes a cognitive radio 4 that detects frequency spectrum 6 within a transmission range of a transmitter 8 of the cognitive device 2. The cognitive radio 4 determines various characteristics (e.g., noise, total bandwidth, unused bandwidth, application, frequency range . . . ) of the detected spectrum and recommends a transmission spectrum (and protocol, power, coding scheme . . . ) for the transmitter 8 based at least in part on the characteristics. The characteristics define a bandwidth opportunity to transmit signals.

The selected transmission spectrum can be associated with various networks such as wireless a cellular network, a Wide Area Network (WAN), a Local Area Networks (LAN), a Metropolitan Area Network (MAN), a Campus Area Network (CAN), a Home Area Network (HAN), a Personal Area Networks (PAN), and the like. The cognitive radio 4 continuously (e.g., at some predefined rate) monitors spectrum and dynamically changes parameters (e.g., the transmission spectrum, protocol, coding scheme . . . ) based on interaction with the environment in which it operates. This interaction can involve active negotiation or communications with other spectrum users and/or passive sensing and decision making within the radio 4. The cognitive radio 4 provides the transmission spectrum recommendation and the spectrum characteristics to a cognitive monitor 10.

The cognitive monitor 10 is an intelligent system that decides what monitored information will be communicated by the transmitter 8. The decision making involves understanding monitoring parameters, a patient's condition, and the environment. The cognitive monitor 10 receives information (e.g., sensed signals, personal information . . . ) from one or more sensors 12 or emitters 14 residing on an individual's body through a Body Area Network (BAN) 16. The sensors 12 collect information such as an Electrocardiogram (ECG), an Electroencephalogram (EEG), an Electromyogram (EMG), a non-invasive blood pressure (NiBP), pulse, respirations, blood oxygen (SpO2), core body temperature, etc. The emitters 14 transmit an individual's identification, current medications, scheduled procedures, etc. In some aspects, devices (not shown) that sense environmental information communicate such information to the BAN.

After collecting this information, the cognitive monitor 10 analyzes the signals. Such analysis includes fusion techniques such as verifying blood pressure using ECG signals to identify erroneous signals (artifacts), which are ignored or discarded. In addition, the analysis includes parsing the received information into one or more groups of related information such as grouping ECG signals, etc. Grouped signals are compared for consistency with each other, and signals deemed inconsistent with the group are discarded or ignored. The cognitive monitor 10 sorts these signals according to quality; artifact-free signals are deemed higher quality signals and signals with artifacts are deemed lower quality signals. In one example, the cognitive monitor 10 selects signals to transmit based on the sorted (or ranked) signals and the recommended transmission spectrum provided by the cognitive radio 4. It is to be understood that the cognitive monitor 10 can receive and use additional information to facilitate selecting signals to transmit. The transmitter 8 sends the selected signals over the transmission spectrum. The cognitive device 2 monitors individuals in various states or conditions. For example, the cognitive device 2 monitors post-operative recovery patients, geriatric patients, mentally ill individuals, depressed individuals, infants susceptible to Sudden Infant Death Syndrome (SIDS), individuals prone to allergic reactions, etc. Non clinical applications include wellness monitoring using application specific modules depending on an individual's concerns.

The cognitive device 2 preferably employs a platform that is universal to different markets throughout the world. This enables the cognitive device 2 to operate as an "always on" monitoring device irrespective of the individual's location. Such pervasiveness allows alarm reporting to be tailored per-person and such alarms can be communicated throughout the world. The actual periodicity of operation (checking available spectrum, receiving signals from the BAN, transmitting signals ...) and quantity of information transmitted is individual specific. Factors considered when determining a duty cycle and volume of information include, but are not limited to, cost, location, sensed physiological signals, the individual's condition, channel noise, quality and reliability, interference, average length of time the spectrum remains unused, and available bandwidth. Examples of suitable modes of operation include continuous, on-demand and emergency only.

By way of example, the following description focuses on a cognitive device that is configured to monitor a post-operative patient. When the patient is at home, the cognitive device 2 leverages a low-use home wireless network (e.g., the patient's personal wireless network or a network in a neighboring house). Since such network commonly is associated with a relatively large percentage of unused bandwidth, signals deemed at least remotely relevant to the patient's recovery are conveyed to a monitoring system accessible to the monitoring clinicians. Depending on the procedure (e.g., coronary bypass surgery, ACL ...), the relevant signals are transmitted every couple minutes, hourly, daily, weekly, etc. When the patient is travelling in a vehicle, the transmission spectrum shifts to an available spectrum. In one instance, this new transmission spectrum is within a cellular network. Since such networks typically are high-use networks, the cognitive device 2 determines that only the most important of these signals should or can be transmitted. In addition, safety measures (e.g., internal memory, buffers ...) are activated for emergency situations such as when there is no suitable unused bandwidth available or when bandwidth being used by the cognitive device 2 is required by the owner of bandwidth. If while travelling in the vehicle a low-use or high-bandwidth spectrum becomes available, the cognitive device 2 increases the amount of signals and frequency with which they are sent. In another example, the patient needs to return to the hospital due to post-operative complications. When entering the hospital's coverage area, the cognitive device 2 transmits clinically relevant signals and patient information to expedite admitting and caring for the patient.

Figure 2:
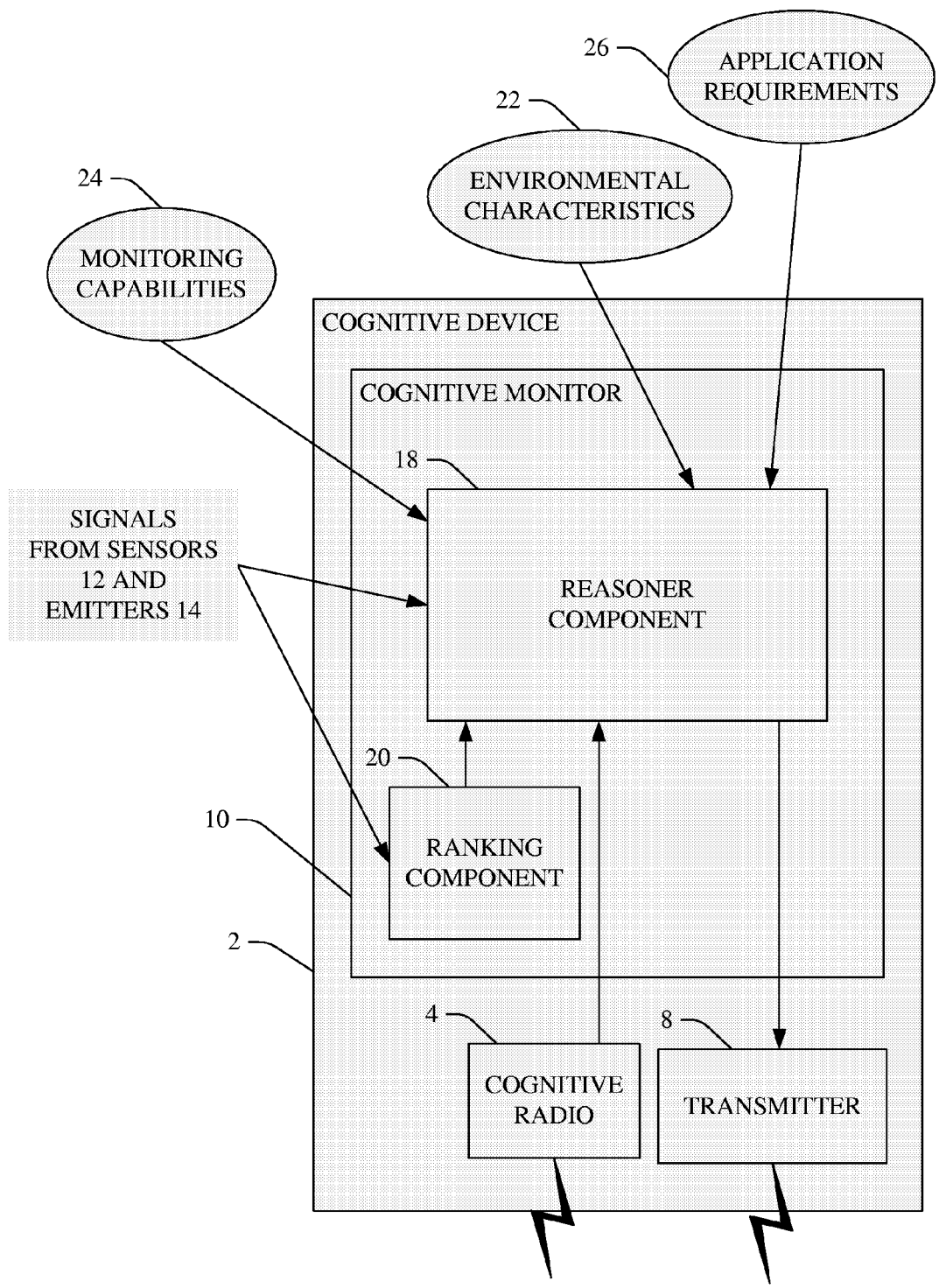
FIG. 2 illustrates an embodiment of the cognitive monitor having a cognitive monitor reasoner component that determines the signals to transmit.

FIG. 2 illustrates an embodiment of the cognitive monitor 10 having a cognitive monitor reasoner component 18 that determines which signals to transmit. As noted previously, the cognitive monitor 10 receives signals indicative of physiological state, an individual's identification, the environment, etc., and selects which signals to transmit based on a signal ranking and the transmission spectrum. Such selection is accomplished through the cognitive monitor reasoner component 18. For example, the physiological signals from the sensors 14 are analyzed by a ranking component 20. This analysis includes distinguishing clinically viable signals (artifact-free signals) from erroneous signals (artifacts), and sorting the signals based on quality. The ranking component 20 provides the ranked signals to the cognitive monitor reasoner component 18. Concurrently, the cognitive radio 4 determines various characteristics (e.g., noise, bandwidth, unused bandwidth, application, frequency range ...) of detected frequency spectrums and provides the cognitive monitor reasoner component 18 with one or more recommendations of available spectrum for transmission by the transmitter 8. The cognitive radio 4 also provides the spectrum characteristics to the cognitive monitor reasoner component 18. It is to be appreciated that such information can be expressed in XML.

The cognitive monitor reasoner component 18 can receive and use additional information to facilitate determining which signals to transmit. For instance, in one embodiment the cognitive monitor reasoner component 18 receives environmental characteristics 22 describing the current usage environment. Such characteristics captures information about location, time, temperature, inputs from a variety of sensors, and information describing the circumstances (e.g., ambulance, home, office, emergency room ...) and so forth. In another embodiment, the cognitive monitor reasoner component 18 checks monitoring capabilities of the monitoring devices within the BAN and at a destination. These capabilities describe monitoring devices such as Fetal Transducer Unit, and can be described using the Composite Capabilities/Preference Profile (CC/PP) recommendation from World Wide Web Consortium (W3C).

In yet another embodiment, the cognitive monitor reasoner component 18 receives application requirements 26 describing relationships amongst different monitoring data. For example, the application requirements 26 can describe rules that facilitate determining the data to communicate under particular circumstances. For instance, the rules may indicate all sensed or monitored data should be communicated if available unused bandwidth surpasses a defined threshold, or only the SpO2 and one ECG lead data should be sent if the available unused bandwidth is within a particular range. The rules can be tailored to an attending clinician such that when that clinician monitors the individual, signals deemed clinically relevant to that clinician will be readily available. Furthermore, these requirements capture clinical constraints based on interaction amongst organs and patient's conditions. For instance, it will capture the relationship between ECG and SpO2, ECG and blood pressure, and blood pressure and SpO2. These requirements can be expressed in a Web Ontology language (OWL) recommendation from W3C.

It is to be appreciated that any or all of this information described above can be stored within the cognitive monitor 2.

For instance, the information can be stored within internal RAM or ROM. The information can also be retrieved by the cognitive monitor 2 or communicated to the cognitive monitor 2 when requested.

The cognitive monitor 2 uses the signal ranking provided by the ranking component 20, the bandwidth recommendation by the cognitive radio 4, the monitoring capabilities 24, the application requirements 26, the environmental characteristics 22, and, optionally, other inputs to determine which signals the transmitter 8 will transmit.

Figure 3:
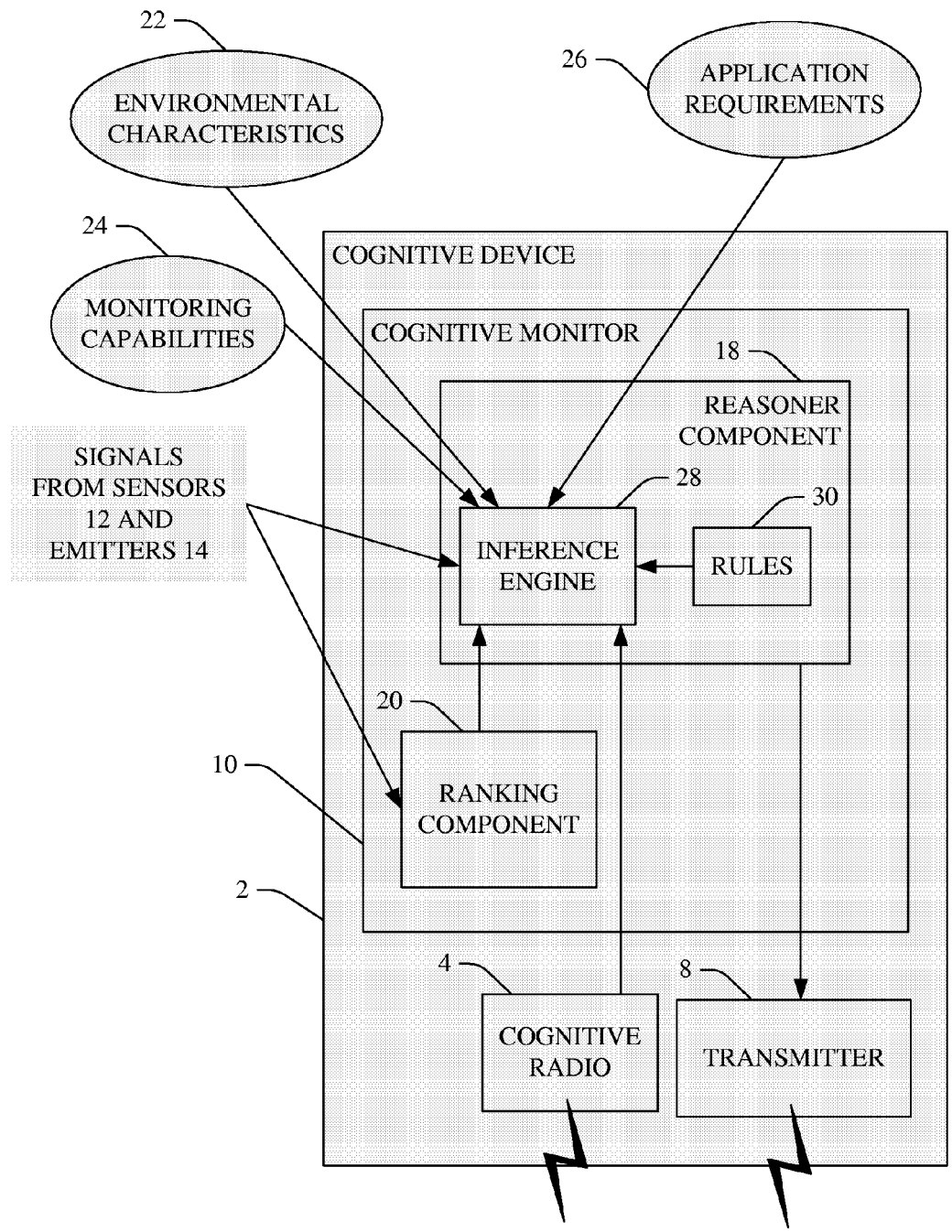
FIG. 3 illustrates an exemplary embodiment of the cognitive monitor reasoner component.

FIG. 3 illustrates an exemplary embodiment of the cognitive monitor reasoner component 18. As depicted, the cognitive monitor reasoner component 18 includes an inference engine 28 and a set of rules 30. The inference engine 28 draws inferences from the information received by the cognitive monitor reasoner component 18 (ranked signals, available transmission spectrum, environmental, characteristics, monitoring capabilities, application requirements . . . ) based on the rules 30. Such inferences determine which signals will be transmitted by the transmitter 8. It is to be appreciated that the inference engine 28 can be a JESS rules engine (a JAVA based rules engine), a neural network, a support vector machine (SVM), a Bayesian classifier, and the like. In addition, the rules 30 include representations of algorithms that a device will employ and can be modelled using Protégé.

Figure 4:
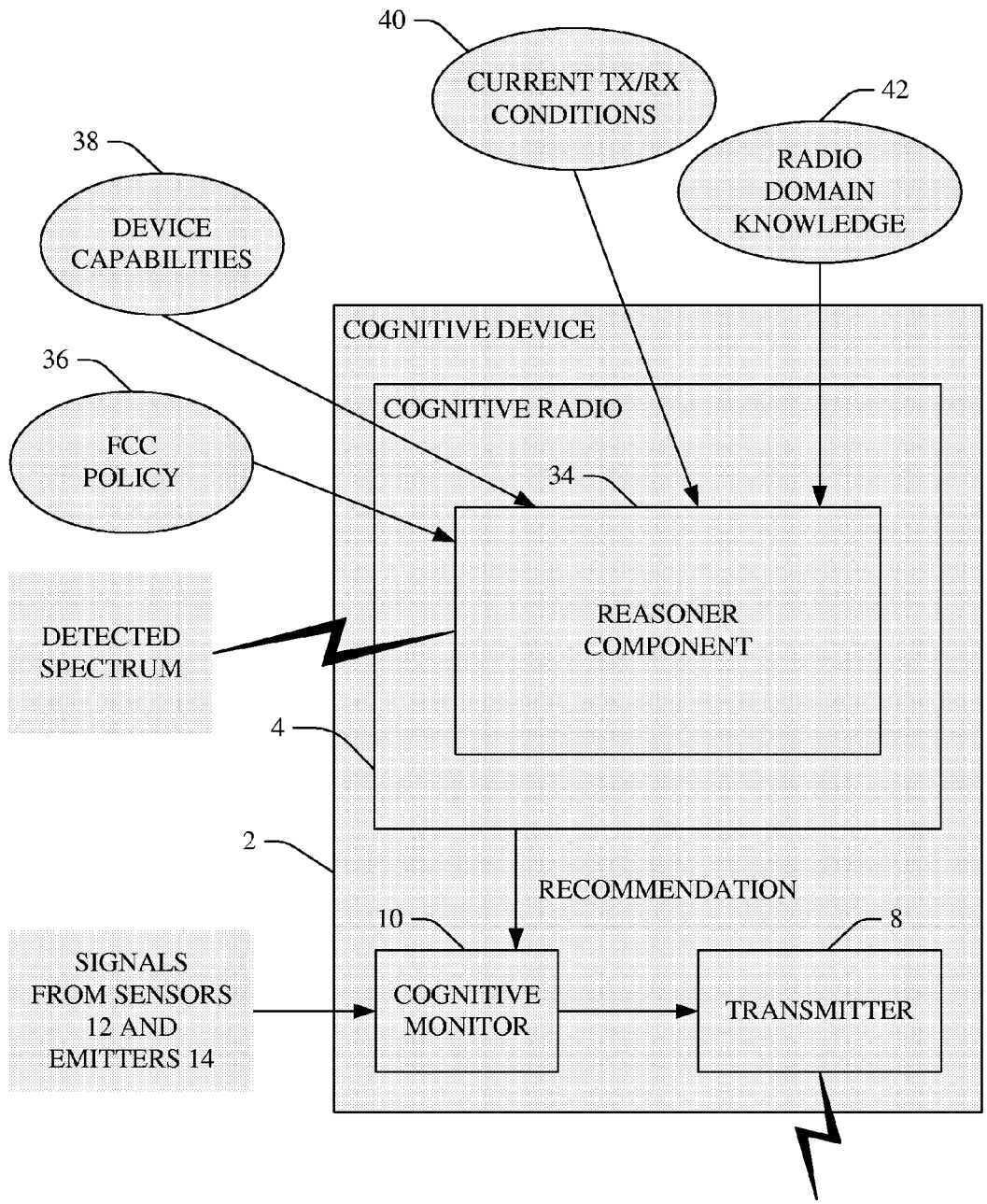
FIG. 4 illustrates an embodiment of the cognitive radio having a cognitive radio reasoner component.

FIG. 4 illustrates an embodiment of the cognitive radio 4 having a cognitive radio reasoner component 34. As described above, the cognitive radio 4 recommends one or more transmission spectrum, transmission protocols, coding schemes, etc. for the transmitter 8 based on spectrum characteristics such as noise, total bandwidth, unused bandwidth, application, frequency range, etc. The cognitive radio reasoner component 34 uses various information to determine this transmission spectrum. For example, in one embodiment the cognitive radio reasoner component 34 uses an FCC policy description 36, which describes the constraints on transmission parameters to limit the level of interference perceived by primary radio systems in the respective area close to the secondary radio system. Such policy typically is represented in the OWL language. In another embodiment, the cognitive radio reasoner component 34 take into consideration device capabilities 38 that describe the characteristics and limitations of the device such as its source of electrical power, CPU, memory, frequency range, channelization, modulation and coding scheme, and communication protocols, for example. Such capabilities can be described using the CC/PP recommendation from W3C.

In yet another embodiment, current transmission/reception (Tx/Rx) conditions 40, which describe the feedback from Media Access Control (MAC) and physical layers about the condition of the transmission environment (noisy, low chatter, . . . ), are analyzed by the cognitive radio reasoner component 34. Measurement results can be provided through known measurement reports such as defined in the IEEE 802.11h and IEEE 802.11k standards using the OWL language. In still another embodiment, radio domain knowledge 42 is made accessible to the cognitive radio reasoner component 34. The radio domain knowledge 42 is a repository of knowledge about the domain of radio communication. Examples of such knowledge includes: algorithms for spectrum opportunity management typically require information about how transmission parameters such as transmission power, frequency, maximum distances between communicating radio devices, modulation technique and coding scheme, etc. are related to each other. The cognitive radio reasoner component 34 may have to know that if the device increases the transmission power, the detection range increases (the distance to the intended receiving device increases), and at the same time the level of interference that other radio devices would observe increases as well.

The cognitive radio reasoner component 34 uses the above information to recommend to the cognitive monitor 8 a transmission frequency spectrum for the transmitter 8. This recommendation describes parameters for transmission such as frequency, maximum allowed power, coding scheme, a protocol, etc. This information can be represented as an XML document/string, provided to the cognitive monitor 10, and used by the cognitive monitor reasoner 18 of the cognitive monitor 10 as described above.

Figure 5:
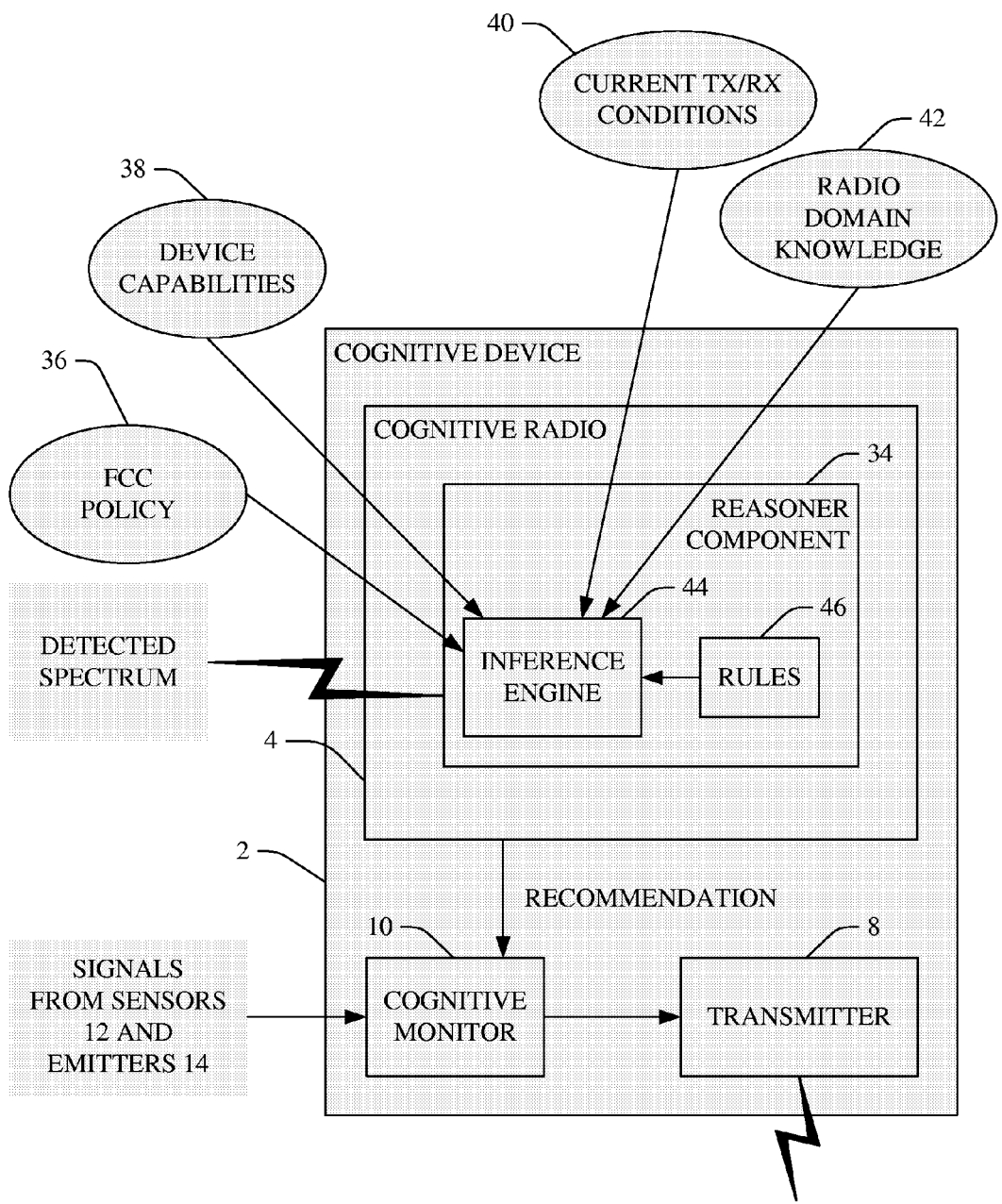
FIG. 5 illustrates an exemplary embodiment of the cognitive radio reasoner component.

FIG. 5 illustrates an exemplary embodiment of the cognitive radio reasoner component 34. The cognitive radio reasoner component 34 includes an inference engine 44 and a set of rules 46. The inference engine 44 draws inferences from the information received by the cognitive radio reasoner component 34 (e.g., FCC policies, device capabilities . . . ) based on the rules 46. These inferences facilitate recommending transmission spectrum for use by the cognitive monitor 10. The inference engine 44 can be a JESS rules engine (a JAVA based rules engine), a neural network, a support vector machine (SVM), a Bayesian classifier, and the like. In addition, the rules 46 include representations of algorithms that a device will employ and can be modelled using Protégé.

The invention claimed is:

1. A patient monitoring system comprising:
   a wireless body area network including:
      at least one sensor that senses physiological information from a patient and wirelessly sends the physiological information on the wireless body area network; and
      a cognitive device which receives the physiological information from the wireless body area network and wirelessly communicates the physiological information to a remote location, the cognitive device including:
         a cognitive radio which monitors an RF frequency spectra including frequency spectra assigned to a primary user for unused bandwidth, and identifies one or more available RF bands not in use by the primary user on which to transmit to the remote location, wherein the cognitive radio selects among the identified available RF bands from the spectrum based in part on a quantity of unused bandwidth available;
         a cognitive monitor which receives the physiological information from the wireless body area network, the cognitive monitor including one or more computing devices programmed to: parse the received physiological information into one or more groups of related physiological information, compare the related physiological information within each group for consistency, determine a degree of artifacting in the received physiological information, prioritize the physiological information based at least in part on a set of rules which prioritize the received information based on at least one of: a physiological condition of the patient, clinical events deemed relevant to a monitoring clinician, and the degree of artifacting, and select which physiological information to transmit based on (1) the prioritization and (2) the available RF bands identified by the cognitive radio;
         an RF transmitter controlled by the cognitive monitor to transmit the selected physiological information as a function of priority over at least one of the identified available RF bands; and a buffer for buffering the physiological information and which is activated in response to no suitable unused bandwidth being available, wherein the cognitive monitor determines a level of noise in the received information and prioritizes the received information with the received information with the least amount of noise having a highest prioritization and the received information with the greatest amount of noise having a lowest prioritization.

2. The patient monitoring system as set forth in claim 1, wherein the cognitive radio continuously checks the RF spectra and dynamically updates the cognitive monitor with the available RF bands.

3. The patient monitoring system as set forth in claim 2, wherein the one or more computing devices is further programmed to: periodically analyze the physiological information remaining to be transmitted and the available RF bands, and re-prioritize the physiological information for transmission based on the available RF bands and the physiological information remaining to be transmitted.

4. The patient monitoring system as set forth in claim 1, the cognitive radio includes:
a reasoner component that analyzes spectrum characteristics of the available RF bands to determine on which available RF band to transmit.

5. The patient monitoring system as set forth in claim 4, wherein the characteristics include at least one of noise, total bandwidth, unused bandwidth, application, and frequency range.

6. The patient monitoring system as set forth in claim 4, the reasoner component includes:
a set of rules representing algorithms; and
one or more computing devices programmed to draw inferences from at least one of a FCC policy, a device capability, a current transmission/reception condition, and radio domain knowledge based on the rules to select the RF band to transmit.

7. The patient monitoring system as set forth in claim 1, the cognitive monitor includes:
a ranking component that ranks the physiological information received from the patient monitoring network based on quality; and
the one or more computing devices is further programmed to prioritize the physiological information based on ranking of the physiological information.

8. The patient monitoring system as set forth in claim 7, wherein the set of rules represent algorithms.

9. A cognitive device for use in the patient monitoring system as set forth in claim 1.

10. A cognitive device that receives physiological information from a patient monitoring network, comprising:
a cognitive radio which monitors RF frequency spectra also used by one or more other users for unused RF bands and characteristics of the unused RF bands including noise and bandwidth, and which identifies one or more available RF bands on which to transmit to a remote location and identifies constraints on transmission parameters for the available RF bands to limit interference with RF transmission of the other users of the RF spectrum, wherein the transmission parameters include frequency, maximum power, coding scheme, and protocol described in a XML document;
a buffer memory;
one or more computing devices programmed to:
parse physiological information received from the patient monitoring network into one or more groups of related physiological information,
compare the related physiological information within each group for consistency,
determine a degree of artifacting in the received physiological information,
prioritize the physiological information based at least in part on a set of rules which prioritize the received information based on at least one of: a physiological condition of the patient, clinical events deemed relevant to a monitoring clinician, and the degree of artifacting, and
select which physiological information to transmit based on the prioritization and the RF bands identified by the cognitive radio as being available,
buffer the physiological information in the buffer memory, when no suitable unused RF bands are available; and
an RF transmitter controlled by the cognitive monitor to transmit the selected physiological information over at least one of the identified available RF bands.

11. A system for conveying physiological information comprising:
one or more sensors which sense the physiological information from a patient and send the sensed physiological information on a body network;
one or more computing devices programmed to:
receive one or more physiological information carrying signals from the body network;
group the physiological information carrying signals based on type;
prioritize the physiological information carrying signals within each group;
prioritize the physiological information carrying groups;
locate RF bands with at least a portion of bandwidth available for transmitting physiological information carried by the signals;
applying rules to draw inferences from at least one of FCC policy, device capability, current transmission reception environment, and radio domain knowledge to determine qualitative and/or quantitative RF transmission characteristics of the located RF bands;
select one or more of the located RF bands with a portion of bandwidth available based on the qualitative and/or the quantitative RF transmission characteristics;
select the physiological information carried by one or more of the physiological information carrying signals to transmit based on (1) the determined prioritization and (2) the RF transmission band characteristics; and
buffer the physiological information in a buffer memory when no suitable unused bandwidth is available;
an RF transmitter which transmits the selected physiological information over the one or more selected RF bands to the remote location.

12. A body coupled network including:
the cognitive device as set forth in claim 10; and
a plurality of sensors which sense the physiological information from a patient and wirelessly transmit the sensed physiological information to the cognitive device.

13. The patient monitoring system as set forth in claim 1 wherein the cognitive radio determines constraints on transmission parameters to limit interferences with RF transmissions by the primary user.

14. The cognitive device as set forth in claim 10, wherein identifying the constraints by the cognitive radio includes applying rules which draw inferences from one or more of an FCC policy, current transmission/reception conditions, and radio domain knowledge.

15. The cognitive device as set forth in claim 10 wherein cognitive radio continuously checks the RF frequency spectra for transmissions by the other users and changes the constraints on the transmission parameters in response to the transmissions by other users.

16. The system as set forth in claim 11 wherein the qualitative and/or quantitative transmission characteristics are determined by drawing inferences from a user of FCC policy, device compatibility, transmission/reception environment, and radio domain knowledge.

17. The system as set forth in claim 11 wherein at least some of the RF bands are shared with other users and wherein the one or more computing device is further programmed to:

determine constraints on transmission parameters for RF transmissions on the selected RF band to limit interference with transmissions of other users; and continuously monitor for transmissions by others and dynamically update at least one of the selected RF band and the determined constraints.

18. The patient monitoring system as set forth in claim 10, wherein the one or more computing devices is further programmed to: periodically analyze the physiological information remaining to be transmitted and the available RF bands, and re-prioritize the physiological information for transmission based on the available RF bands and the physiological information remaining to be transmitted.

19. The patient monitoring system as set forth in claim 11, wherein the one or more computing devices is further programmed to: continuously analyze the physiological information remaining to be transmitted and the available RF bands, and re-prioritize the physiological information for transmission based on the available RF bands and the physiological information remaining to be transmitted.

* * * * *